United States Patent
Modglin et al.

(10) Patent No.: US 11,129,742 B2
(45) Date of Patent: Sep. 28, 2021

(54) ADJUSTABLE CIRCUMFERENTIAL LENGTH LUMBAR SACRAL BRACE

(71) Applicant: DeRoyal Industries, Inc., Powell, TN (US)

(72) Inventors: Michael D. Modglin, Braselton, GA (US); Karen M. Clements, Knoxville, TN (US); Charles J. French, III, Knoxville, TN (US); Sarah O. Davis, Gonzales, LA (US); Michael R. Galante, Knoxville, TN (US); Gregory S. Hodge, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 705 days.

(21) Appl. No.: 14/133,933

(22) Filed: Dec. 19, 2013

(65) Prior Publication Data

US 2014/0188023 A1    Jul. 3, 2014

Related U.S. Application Data

(60) Provisional application No. 61/746,392, filed on Dec. 27, 2012.

(51) Int. Cl.
*A61F 5/02* (2006.01)

(52) U.S. Cl.
CPC .................... *A61F 5/028* (2013.01)

(58) Field of Classification Search
CPC .......... A61F 5/028; A61F 5/022; A61F 5/024; A61F 5/00; A61F 5/02–03; A61F 5/01; A61F 5/058–05833; A61F 5/24–3792; A41D 13/0525; A41D 13/0531
USPC .......................................................... 602/19
See application file for complete search history.

(56) References Cited

U.S. PATENT DOCUMENTS

| | | | | |
|---|---|---|---|---|
| 4,475,543 A | * | 10/1984 | Brooks | .................... A61L 15/07 |
| | | | | 602/19 |
| 5,388,274 A | | 2/1995 | Glover et al. | |
| 5,690,609 A | * | 11/1997 | Heinze, III | .............. A61F 5/028 |
| | | | | 128/115.1 |
| 7,815,585 B2 | * | 10/2010 | Vollbrecht | .............. A61F 5/028 |
| | | | | 602/12 |

(Continued)

FOREIGN PATENT DOCUMENTS

| | | |
|---|---|---|
| CN | 1311648 A | 9/2001 |
| CN | 101217921 A | 7/2008 |
| DE | 102012011718 A1 | 8/2012 |
| EP | 2223669 A1 | 11/2010 |

OTHER PUBLICATIONS https://www.merriam-webster.com/dictionary/one-piece (last visited Feb. 22, 2021).*

(Continued)

*Primary Examiner* — Alireza Nia
*Assistant Examiner* — Michelle J Lee
(74) *Attorney, Agent, or Firm* — Luedeka Neely Group, PC

(57) ABSTRACT

An adjustable length brace includes an elongate body encircling portion having a free end having an adjustable length; and an end portion releasably attachable to the free end of the body encircling portion. The length of the brace may be adjusted by adjusting the length of the body encircling portion by adjusting the length of the free end of the body encircling portion, and connecting the end portion to the free end of the body encircling portion to adjust the length of the brace.

5 Claims, 7 Drawing Sheets

(56) References Cited

U.S. PATENT DOCUMENTS

| | | | |
|---|---|---|---|
| 8,142,377 B2* | 3/2012 | Garth | A61F 5/028 602/19 |
| 2008/0208090 A1 | 8/2008 | Vollbrecht | |
| 2009/0192425 A1* | 7/2009 | Garth | A61F 5/028 602/19 |
| 2010/0168630 A1 | 7/2010 | Cropper et al. | |
| 2010/0204630 A1* | 8/2010 | Sandifer | A61F 5/026 602/19 |
| 2010/0217167 A1* | 8/2010 | Ingimundarson et al. | 602/19 |
| 2011/0224591 A1 | 9/2011 | Thorgilsdottir et al. | |
| 2013/0030338 A1* | 1/2013 | Hinshon | A61F 5/028 602/19 |

OTHER PUBLICATIONS

International Search Report and Written Opinion, PCT/US2013/076528, dated Mar. 7, 2014—47 pages.

PCT/US2013/076528, The International Bureau of WIPO PCT Notification Concerning Transmittal of International Preliminary Report on Patentability, dated Jul. 9, 2015 (1 page).

PCT/US2013/076528, The International Bureau of WIPO International Preliminary Report on Patentability dated Jun. 30, 2015 (5 pages).

State Intellectual Property Office of People's Republic of China, Search Report 201380068602.4 First Search.

* cited by examiner

ADJUSTABLE CIRCUMFERENTIAL LENGTH LUMBAR SACRAL BRACE

CROSS-REFERENCE TO RELATED APPLICATION

This application claims priority to U.S. Provisional Application No. 61/746,392 filed on Dec. 27, 2012, and entitled ADJUSTABLE CIRCUMFERENTIAL LENGTH LUMBAR SACRAL BRACE, incorporated by reference herein in its entirety.

FIELD

This disclosure relates to the field of orthopedic bracing. More particularly, this disclosure relates to adjustable circumferential length lumbar sacral braces.

BACKGROUND

Improvement is desired in the provision of soft and flexible braces for supporting the thoraco-lumbro-sacral spine. While conventional lumbar belt type braces provide support, improvement is desired in providing a soft and flexible lumbo-sacral brace to which can be added desired rigidity in an anterior, posterior and lateral portion of the belt adjacent the spine, and which is adjustable to fit a wide range of waist sizes circumferentially. The benefit of the flexibility of this brace design is a reduction of a large inventory of various sizes.

The disclosure relates to an adjustable brace system, and in particular, adjustable circumferential length lumbar sacral braces.

SUMMARY

The above and other needs are met by an adjustable circumferential length spinal brace that can be used with a variety of waist sizes to reduce the need to carry an inventory of different waist sized spinal braces. The brace is also configured so that rigid or semi-rigid components can be added to control movement in the entire thoraco-lumbo-sacral region of the spine. The brace includes a posterior portion and a pair of opposite end portions releasably attachable to the posterior portion. The posterior portion may have a sleeve, pocket or flap into which is positioned an adjustable length member and a rigid or semi-rigid stay.

To adjust the length of the adjustable length member, one or both free ends of the adjustable length member are folded back and the free ends are secured to the adjustable length member to maintain the folded orientation of the free ends that are folded. Alternatively, cutting or removal of the extra material may be done at the choice of the fitter of the brace. The brace may further include a tensioning system, such as a cable tensioning system, on one or both of the end portions.

In another aspect, the disclosure provides an adjustable length brace that includes an elongate body encircling portion having a free end having an adjustable length; and an end portion releasably attachable to the free end of the body encircling portion. The length of the brace may be adjusted by adjusting the length of the body encircling portion by adjusting the length of the free end of the body encircling portion, and connecting the end portion to the free end of the body encircling portion to adjust the length of the brace.

In yet another aspect, the disclosure provides an adjustable length brace, including an elongate body encircling portion having opposite free ends, each of the free ends having an adjustable length; and a pair of end portions, each of the end portions being releasably attachable to one of the free ends of the body encircling portion.

The length of the brace may be adjusted by adjusting the length of the body encircling portion by adjusting the length of one or both of the free ends of the body encircling portion, and connecting the end portions to the free ends of the body encircling portion to adjust the length of the brace.

Braces according to the disclosure are advantageous as compared to prior devices. For example, other designs that also offer a modular nature of adding components to extend support above the lumbo-sacral region to cover also the thoracic region have a single adjustment zone that opens in the posterior or back portion of the brace. These designs can easily pinch the skin or cause friction and post surgically cause pain at the incision site which is normally in that posterior region. Additionally if post surgically drainage tubes have been placed in the incision site or sites as is typical, that type of design could easily pull or dislodge the drainage tubes.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
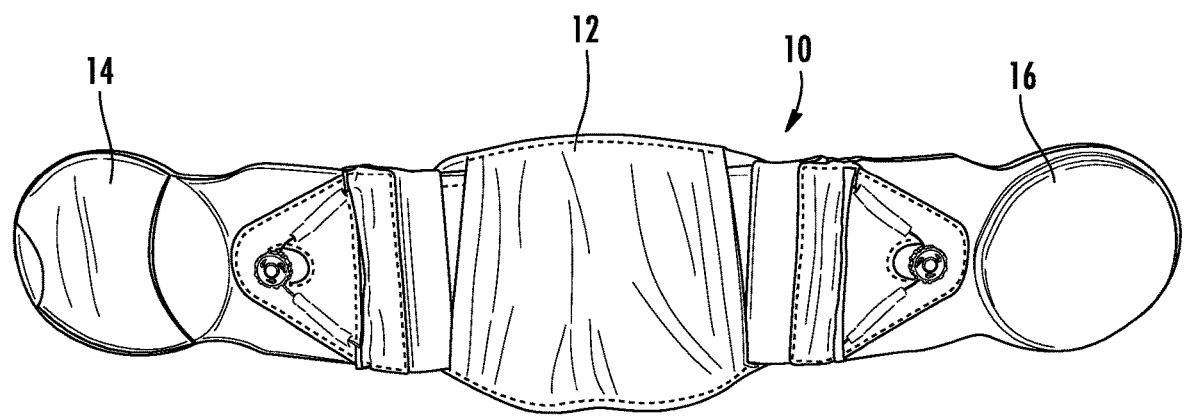
FIG. 1 is a front plan view of an adjustable brace according to the disclosure.
Figure 2:
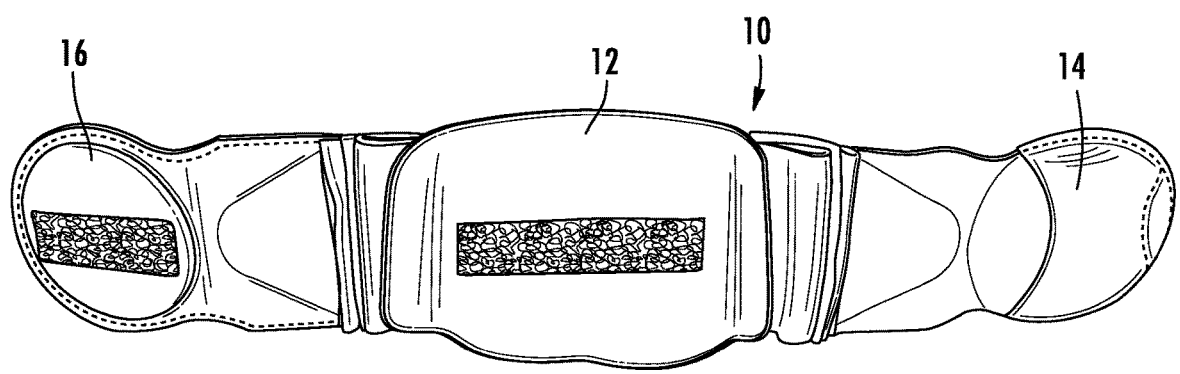
FIG. 2 is a rear plan view of the adjustable brace of FIG. 1.
Figure 3:
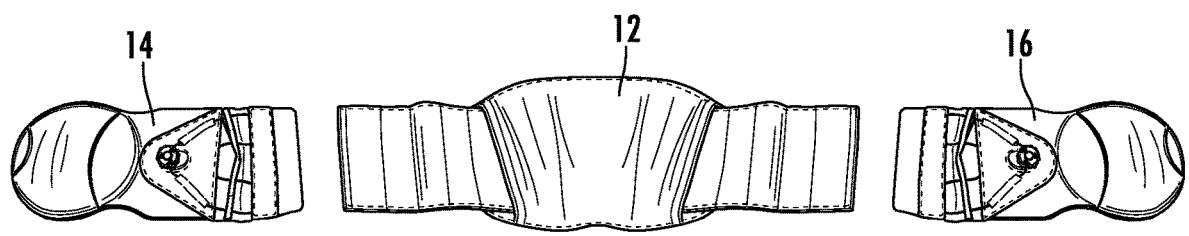
FIG. 3 is a frontal partially exploded view of the brace of FIG. 1.
Figure 4:
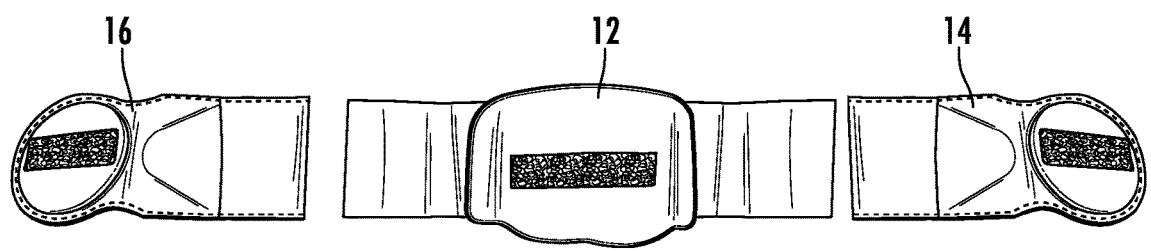
FIG. 4 is a rear partially exploded view of the brace of FIG. 1.

With initial reference to FIGS. 1-5, there is shown an adjustable length lumbar sacral brace 10. The brace 10 includes a posterior portion 12 and a pair of opposite end portions 14 and 16 releasably attachable to the posterior portion 12.

While the disclosure describes the construction of a lumbo-sacral belt, it will be appreciated that rigid or semi-rigid components may be added anteriorly, posteriorly, or laterally to the described brace to increase stability into the thoracic or even the cervical spine so that a patient can be treated with one brace as they progress through different stages of treatment or healing.

The brace 10 is configured for installation around the waist of a user. To accomplish this, the posterior portion 12 is placed adjacent a posterior of the spine of the user, with the ends 14 and 16 attached to the posterior portion 12. The ends 14 and 16 are then urged forward around the sides of the user and are overlapped at the anterior of the user and connected to one another to secure the brace in position.

The posterior portion 12 includes an adjustable length member 18 having free end portions 18a and 18b, to which the end portions 14 and 16 connect. As described below, the length the adjustable length member 18 is adjusted by folding one or more of the free end portions 18a and 18b to adjust the length of the brace 18.

Figure 5:
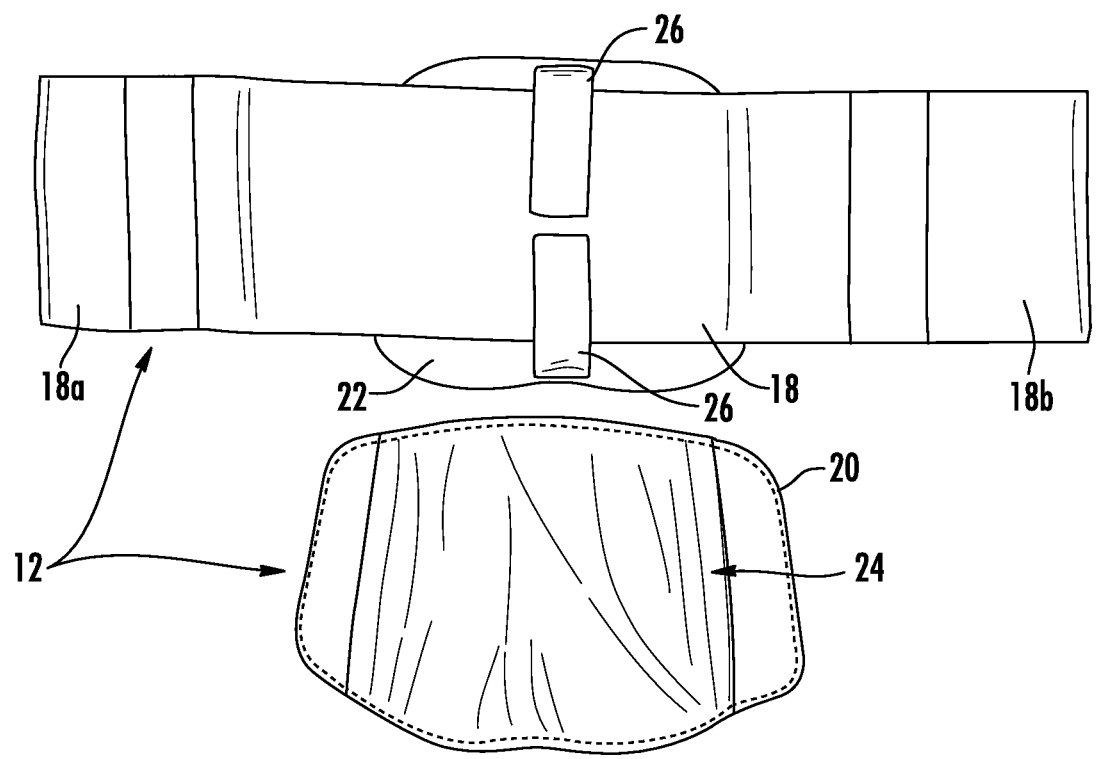
FIG. 5 is a partially exploded view of a posterior component of the brace of FIG. 1.
Figure 6:
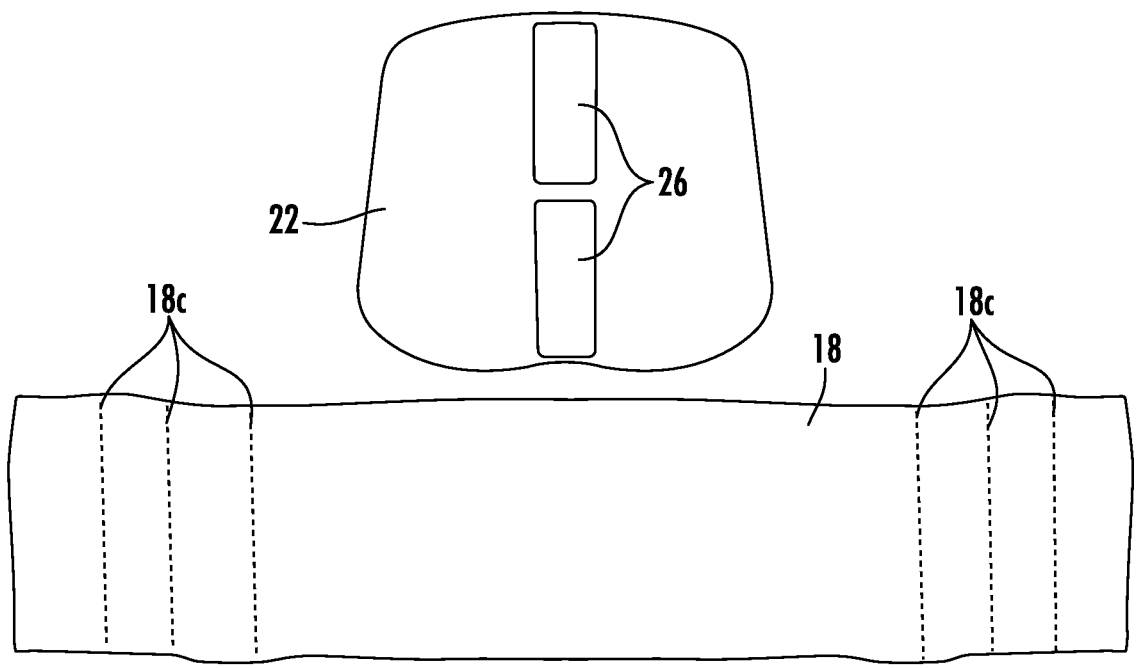
FIG. 6 is an exploded view of an adjustable member of the posterior component of the brace of FIG. 1.

With reference to FIG. 5, the posterior portion 12 further includes a flap, pocket, or sleeve 20. The adjustable length member 18 passes through the sleeve 20 and a rigid or semi-rigid stay 22 is positioned within the sleeve 20.

The adjustable length member 18 is an elongate and flexible member preferably made of a soft fabric surrounding a batting or padding, such as a soft foam or spacer fabric. The soft fabric is desirably functional as a loop material for matingly and releasably engaging a hook material to facilitate a hook and loop type attachment with the end portions 14 and 16, as explained below. The end portions 18a and 18b may be made of the same material as the adjustable length member 18, the material used to provide the exterior of the end portions 18a and 18b is desirably functional as a loop material for matingly engaging hook material.

To provide the brace 10 with the ability to adjust between waist sizes of from about 26 inches to about 60 inches, the adjustable length member 18 has an overall length of about 30 inches, with each of the end portions 18a and 18b being about 15 inches in length. To facilitate folding of the end portions 18a and 18b for adjustment of the length of the adjustable length member 18, each end portion 18a and 18b may include defined fold or cut lines 18c spaced a uniform distance apart of from about 1 to about 2 inches. To adjust the effective length of each of the end portions 18a and 18b, each of the end portions 18a and 18b may be folded or cut such as at a selected one of the lines 18c.

The sleeve 20 is configured to be positioned adjacent the posterior lumbo-sacral region of the user and to define a channel 24 for receiving the adjustable length member 18 and the stay 22. The sleeve 20 is conformable and padded for comfort to the user, and may be made of a soft fabric surrounding a soft foam or padding. The stay 22 is made of a lightweight but substantially rigid material, such as a polyethylene or the like, and configured to be positioned inside the channel 24 so as to be adjacent the posterior of the user for providing support. The stay 22 may include rivets or other fasteners, such as strips of hook material 26 fixedly connected to the stay 22. The hook material 26 is configured to matingly and releasably engage loop material of the adjustable length member 18 proximate a central portion of the adjustable length member 18 to affix the adjustable length member 18 to the stay 22. As will be appreciated, other fastening devices may be utilized.

The posterior portion 12 is assembled by positioning the adjustable length member 18 lengthwise across the stay 22 and securing the central portion of the member 18 to the stay 22 using the hook material 26. This assembly is then inserted into the channel 24 of the sleeve 20 so that the end portions 18a and 18b extend outwardly from the sleeve 20 along the posterior of the user. As will be appreciated, the adjustable length member 18 could be exposed and not within an enclosing structure such as the sleeve 20, but the sleeve 20 simply represents one manner of construction.

Figure 7:
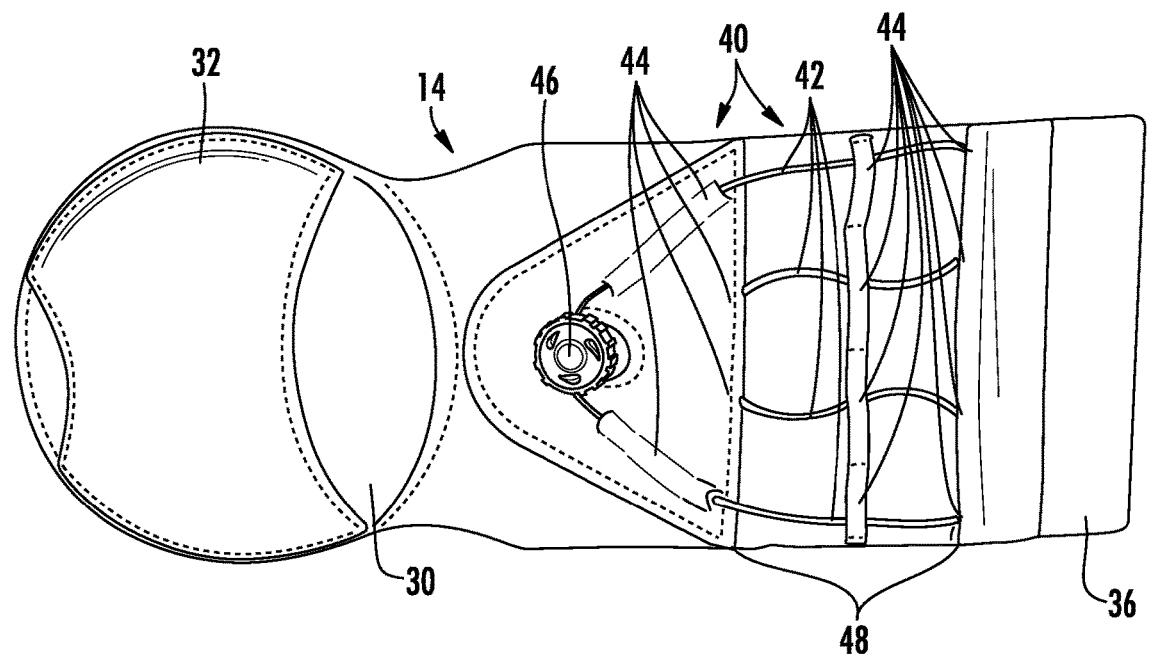
FIG. 7 is a front plan view of an end portion of the brace of FIG. 1.
Figure 8:
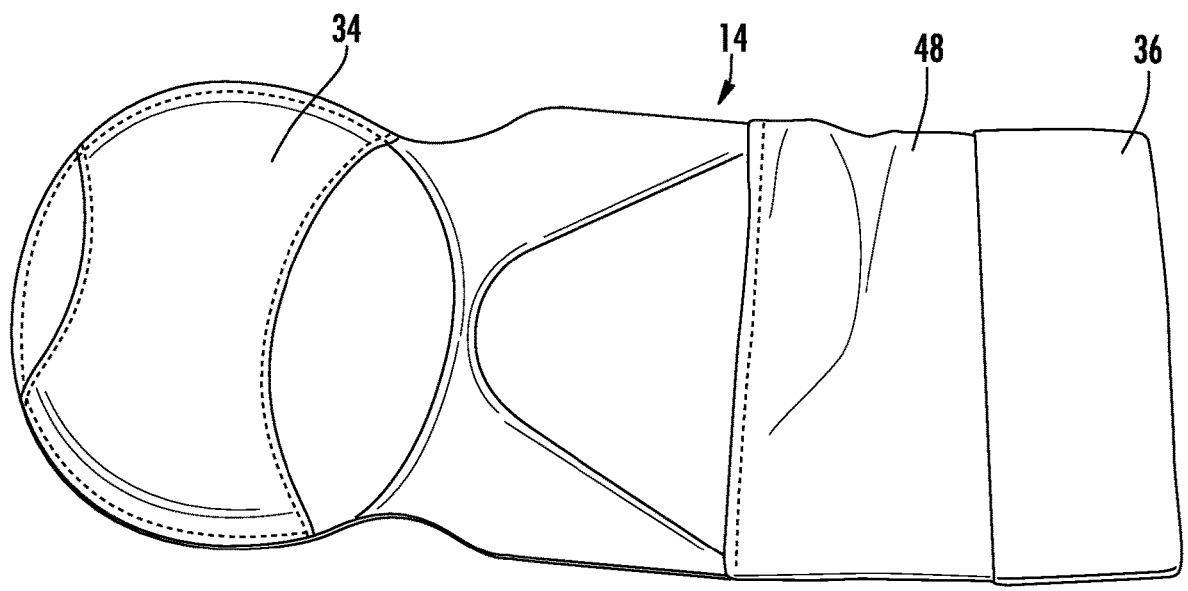
FIG. 8 is a rear plan view of an end portion of the brace of FIG. 1.

With reference to FIGS. 7 and 8, the end portion 14 is provided by a length of flexible material, such as a soft fabric surrounding a padding or soft foam. The end portion 14 includes a head 30 configured for overlapping with a corresponding head of the end portion 16. The head 30 includes a hand grip 32 on a front side thereof configured for grasping by the user and a hook/loop fastener 34 on a back side thereof for mating with a corresponding loop/hook fastener of the end portion 14. A tail 36 of the end portion 14 is opposite the head 30 and may be provided as a segment of hook material for matingly engaging the loop material of the end portion 18a of the adjustable length member 18. As will be appreciated, the materials may be switched so that the end portion 14 provides a loop material and the end portion 18a of the adjustable length member 18 has hook material. Also, other fastening structures, such as buttons and apertures, may be used instead of hook and loop materials for releasably securing the end portions 18a of the adjustable length member 18 to the end portions 14 and 16.

The end portion 16 is substantially identical to the end portion 14, and the end portion 14 and the end portion 16 may each have a length of about 18 inches for use with the adjustable length member 18 having a length of about 30 inches to enable use with waist sizes ranging from about 26 inches to about 60 inches.

Figure 9:
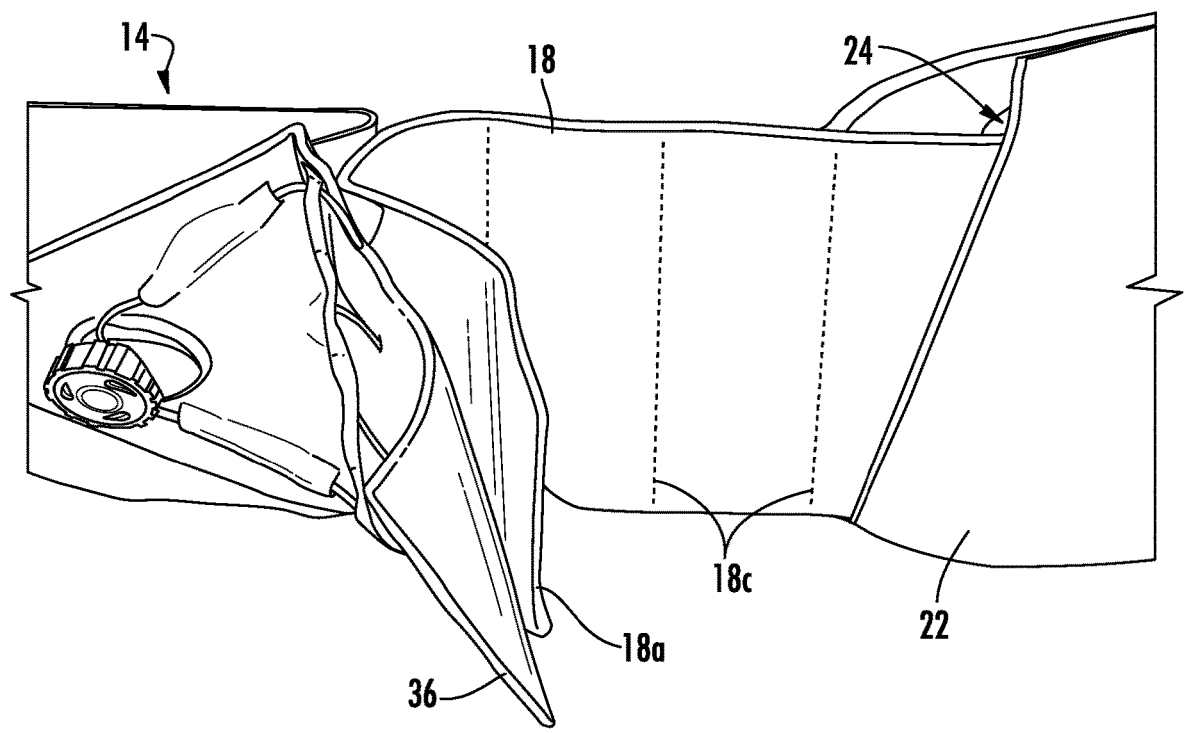
FIGS. 9 and 10 show adjustment of the adjustable member to adjust the length of the brace of FIG. 1.
Figure 10:
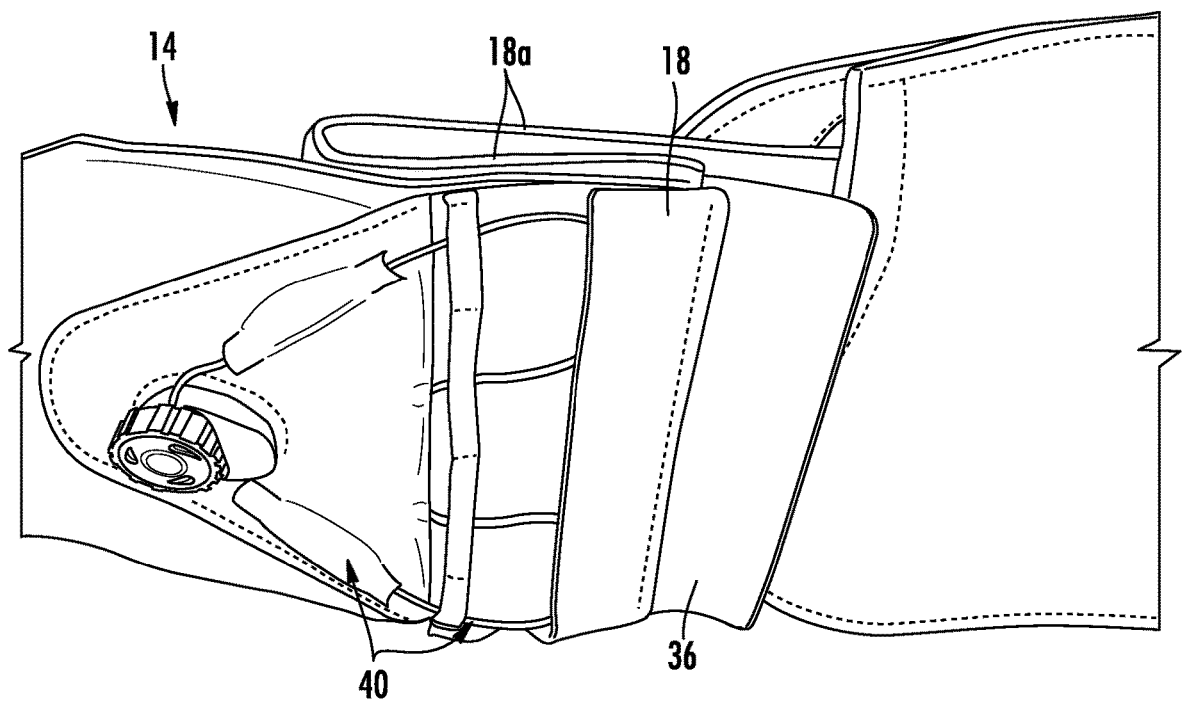

With reference to FIGS. 9 and 10, the length of the brace 10 may be adjusted by adjusting the length of the adjustable length member 18 and connecting the end portions 14 and 16 to the member 18 to fix the length of the member 18, and thereby adjust the length of the brace 10. The length of the member 18 is at its maximum when the member 18 is fully extended. To adjust the length of the member 18, one or both of the end portions 18a and 18b are folded back and against the adjustable length member 18 and the end portions 14/16 are secured to the member 18 to maintain the folded orientation of the end portion 18a and/or end portion 18b that is folded. As mentioned previously, the end portions 18a and 18b may be cut to a reduced length instead of being folded.

If desired, further adjustability of the brace 10 may be provided by including a tensioning system 40 on the end portion 14 or the end portion 16 or both. The tensioning system 40 is preferably a cable tensioning system and includes a cable 42, cable guides 44, and a cable take-up 46. For use with the cable tensioning system 40, the end portion 14 preferably includes an intermediate portion 48 of the end portion 14 provided as by a single fabric layer so as to be able to be drawn up or compacted in length without undue bulk resulting. The cable 42 spans the intermediate portion and taking up or shortening the cable 42 using the cable take-up 46 compacts or shortens the intermediate portion 48 to enable an additional degree of adjustment of the length of the brace. Other tensioning systems may be used, such as ratchet or other incremental adjustment devices.

In this regard, the adjustment of the adjustable length member 18 as by adjustment of the end portion 18a or the end portion 18b or both enables macro adjustment of the length of the brace, e.g., adjustments of one inch or more. An additional degree of micro adjustment, e.g., adjustment of less than an inch, is provided by the tensioning system 40. A suitable device to provide the cable take-up 46 are cable reel devices available under the name BOA from Boa Technology, Inc. of Denver, Colo., and described in U.S. Pat. Nos. 7,954,204 and 7,992,261, incorporated by reference in their entireties.

As will be appreciated, spinal braces according to the disclosure advantageously enable adjustment of the length of the spinal brace in a manner that provides adjustment at a location that is remote from the posterior or back portion of the brace. Also, the adjustment of the length of the brace is accomplished in a manner that avoids pinching of the skin of the user, and avoids movement of the posterior of the brace. This is advantageous to avoid undesirable dislodgment of drainage tubes or the like located at the incision site of the spine.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. An adjustable length brace, comprising:
  an adjustable length elongate and flexible one-piece body encircling portion made of a soft fabric and having opposite first and second free ends each having a length, the first free end being folded to adjust the length of the first free end and the second free end being folded to adjust the length of the second free end to enable adjustment of the length of the one-piece body encircling portion; and
  first and second end portions, each having a length shorter than the one-piece body encircling portion, the first end portion being releasably attachable to the folded first free end of the one-piece body encircling portion and the second end portion being releasably attachable to the folded second free end of the one-piece body encircling portion, the first and second end portions being connectable to one another; and
  a tensioning system configured to draw up and compact the length of one of the end portions of the brace.

2. The brace of claim 1, wherein the brace is a spinal brace and the one-piece body encircling portion includes a central posterior portion positionable adjacent a spine of a user.

3. The brace of claim 2, further comprising a rigid or semi-rigid stay removably positionable on the posterior portion.

4. The brace of claim 1, wherein the body encircling portion includes an enclosing structure such as a sleeve, pocket, or flap for receiving a portion of the body encircling portion.

5. The brace of claim 1, wherein the tensioning system comprising a cable configured to draw up and compact the length of one of the end portions of the brace.

* * * * *